(12) United States Patent
Wozencroft et al.

(10) Patent No.: US 8,500,744 B2
(45) Date of Patent: Aug. 6, 2013

(54) CAP AND ACTIVATION TOOL

(75) Inventors: Robert Michael Wozencroft, Epsom (GB); Michael Anthony Tuke, Guilford (GB); Nicholas Lee Hawson, Old Leak (GB)

(73) Assignee: Finsbury (Development) Limited, Leatherhead (GB)

( * ) Notice: Subject to any disclaimer, the term of this patent is extended or adjusted under 35 U.S.C. 154(b) by 1415 days.

(21) Appl. No.: 11/383,139

(22) Filed: May 12, 2006

(65) Prior Publication Data

US 2006/0293686 A1    Dec. 28, 2006

(30) Foreign Application Priority Data

May 12, 2005  (GB) .................................. 0509766.2
Sep. 29, 2005  (GB) .................................. 0519865.0

(51) Int. Cl.
*A61F 2/46*    (2006.01)
(52) U.S. Cl.
USPC ......................................... 606/91; 623/22.12
(58) Field of Classification Search
USPC ................. 606/81, 91, 99; 623/22.11–22.12, 623/22.14–22.15, 22.21–22.23
See application file for complete search history.

(56) References Cited

U.S. PATENT DOCUMENTS

| | | |
|---|---|---|
| 186,586 A | 1/1877 | Le Row |
| 3,067,740 A | 12/1962 | Haboush |
| 3,584,318 A | 6/1971 | Scales et al. |
| 3,745,590 A | 7/1973 | Stubstad |
| 3,909,855 A | 10/1975 | Barredo |
| 4,131,116 A | 12/1978 | Hedrick |
| 4,180,873 A | 1/1980 | Fixel |
| 4,244,060 A | 1/1981 | Hoffer |
| 4,351,466 A | 9/1982 | Noiles |
| 4,611,587 A | 9/1986 | Powlan |
| 4,677,972 A | 7/1987 | Tornier |
| 4,712,951 A | 12/1987 | Brown |
| 4,961,748 A | 10/1990 | Frey et al. |
| 5,098,437 A | 3/1992 | Kashuba et al. |
| 5,108,447 A | 4/1992 | Zeiler et al. |
| 5,171,243 A | 12/1992 | Kashuba et al. |
| 5,312,410 A | 5/1994 | Miller et al. |
| 5,376,126 A | 12/1994 | Lin |
| 5,474,560 A | 12/1995 | Rohr, Jr. |
| 5,486,181 A * | 1/1996 | Cohen et al. .................... 606/91 |

(Continued)

FOREIGN PATENT DOCUMENTS

| | | |
|---|---|---|
| DE | 3324103 A1 | 11/1984 |
| DE | 10250390 A1 | 5/2004 |

(Continued)

*Primary Examiner* — Thomas J Sweet
*Assistant Examiner* — Megan Wolf
(74) *Attorney, Agent, or Firm* — Senniger Powers LLP

(57) ABSTRACT

A cap used during the insertion of an acetabular cup prosthesis. The cap includes impaction plate having an upperside and an underside. The impaction plate includes a plurality of separate sectors mutually connected at a connection point on the impaction plate by flanges. Each sector includes interlocking elements which in use enable the impaction plate to be connected to an introduction tool. The cap also includes at least one lug extending downwardly from the underside of each sector. The lug is located at the portion of the underside of the impaction plate which will in use enable the lug to be interconnected with a corresponding recess on an internal wall, an external wall or a rim of a prosthesis.

42 Claims, 7 Drawing Sheets

U.S. PATENT DOCUMENTS

| | | |
|---|---|---|
| 5,531,785 A | 7/1996 | Love et al. |
| 5,534,011 A | 7/1996 | Greene, Jr. et al. |
| 5,540,697 A | 7/1996 | Rehmann et al. |
| 5,549,618 A | 8/1996 | Fleenor et al. |
| 5,549,692 A | 8/1996 | Hauser et al. |
| 5,571,111 A * | 11/1996 | Aboczky .................. 606/91 |
| 5,669,919 A | 9/1997 | Sanders et al. |
| 5,683,399 A * | 11/1997 | Jones ..................... 606/91 |
| 5,702,476 A | 12/1997 | Limacher et al. |
| 5,702,477 A | 12/1997 | Capello et al. |
| 5,752,964 A | 5/1998 | Mericle |
| 5,810,832 A | 9/1998 | Blasingame et al. |
| 5,873,906 A | 2/1999 | Lau et al. |
| 5,904,688 A | 5/1999 | Gilbert et al. |
| 5,928,287 A | 7/1999 | Keller |
| 5,931,870 A | 8/1999 | Cuckler et al. |
| 5,954,727 A | 9/1999 | Collazo |
| 5,976,148 A | 11/1999 | Charpenet et al. |
| 6,022,357 A | 2/2000 | Reu et al. |
| 6,063,123 A | 5/2000 | Burrows et al. |
| 6,168,600 B1 | 1/2001 | Grace et al. |
| 6,451,058 B2 | 9/2002 | Tuke et al. |
| 6,746,452 B2 | 6/2004 | Tuke et al. |
| 2003/0125805 A1 | 7/2003 | Johnson et al. |
| 2003/0220698 A1 * | 11/2003 | Mears et al. ............. 623/22.4 |
| 2004/0073226 A1 * | 4/2004 | Cotting et al. ............ 606/91 |
| 2004/0122450 A1 | 6/2004 | Oren et al. |
| 2004/0148017 A1 | 7/2004 | Stobie |
| 2004/0186586 A1 | 9/2004 | Seyer et al. |

FOREIGN PATENT DOCUMENTS

| | | |
|---|---|---|
| EP | 1634552 A2 | 3/2006 |
| GB | 2323036 A | 9/1998 |
| WO | 04000172 A1 | 12/2003 |

* cited by examiner

Fig. 8.
Fig. 9.
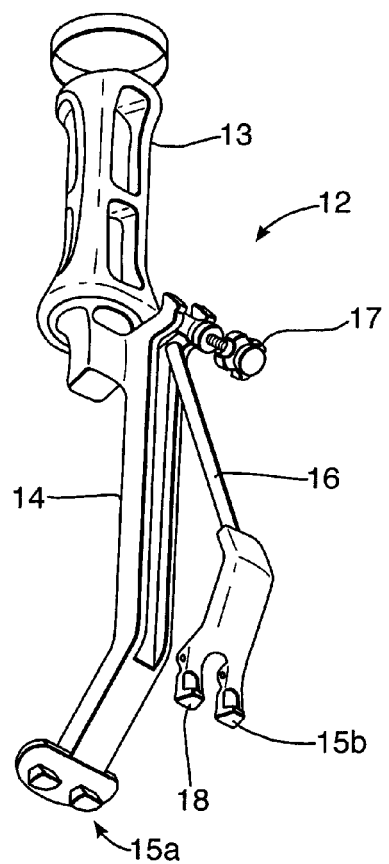
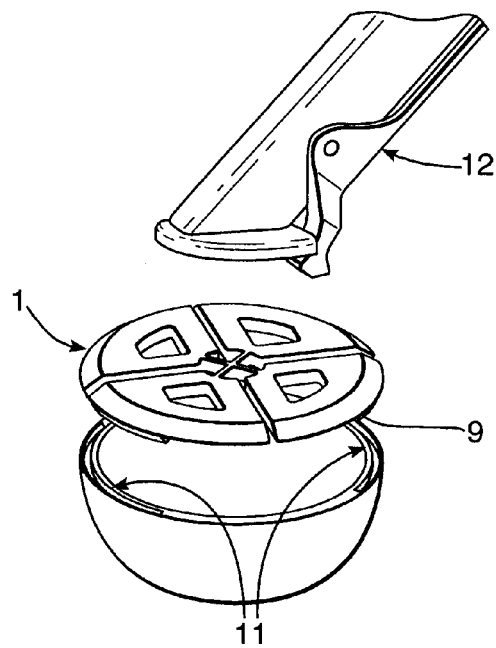
Fig. 10.
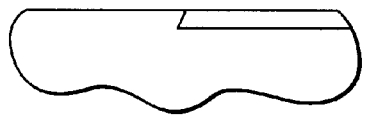

17

CAP AND ACTIVATION TOOL

CROSS-REFERENCE TO RELATED APPLICATIONS

This application claims priority to foreign applications UK Pat. App. No. 0509766.2 filed May 12, 2005, and UK Pat. App. No. 0519865.0 filed Sep. 29, 2005, both of which are hereby incorporated by reference.

BACKGROUND OF THE INVENTION

The present invention relates to a cap for a prosthetic implant particularly a prosthetic acetabulum implant and to an introduction tool for use therewith.

The replacement of all or a part of the bone surface of an articulation with a prosthetic implant has become a common surgical procedure. The procedure requires the surgeon to exercise both precision and delicacy in the placement of the prosthetic implant. However, it is frequently necessary for the surgeon also to exercise a degree of force, sometimes a vigorous force, in order to situate the prosthetic implant in the desired location on the bone surface.

For example, in an operation to insert a prosthetic acetabulum in a patient's pelvis the surgeon first uses a reamer to grind a cavity of appropriate size in the patient's pelvis. An acetabular cup is then inserted into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter, with 2 mm increments between neighboring sizes.

There are a number of different types of prosthetic acetabular cups. One type of cup is made from polyethylene. These are generally cemented into the acetabulum and require only light pressure to seat them in the cement. One alternative cup type has a polyethylene liner unit for articulation with the femur and a metal shell for insertion into the pelvic cavity. These cups with metal shells may be implanted without cement such that they rely on a jam fit between the metal shell and the patient's acetabulum. Often these metal shells have outer surfaces or coatings which encourage bone to grow into them over time. With this type of prosthesis, the polyethylene liner unit is snapped or screwed into the metal shell after the metal shell has been seated in the acetabulum to form the socket part of the joint.

Prosthetic acetabular cups generally require the use of an insertion tool to achieve correct positioning of the prosthesis in the patient's pelvic cavity. Cups which rely on a jam fit require a greater force to be applied via the insertion tool than is the case with cemented polyethylene cups. This force is usually a direct impact into the acetabulum, but force may also be applied to adjust the angular position of the cup or to remove the cup if it has been positioned incorrectly.

In order that the required forces are accurately and safely applied to the cup, it is generally necessary that the insertion tool positively grips the cup. However, it is also important that the means by which the tool grips the cup does not impinge upon the outside of the metal shell in order that in use the insertion tool does not become trapped between the shell and the pelvic bone. Further, as the wall thickness of the shell is generally kept to a minimum, the tool cannot generally grip the wall. Insertion tools are therefore generally designed to grip on a mechanical feature provided on the inner hemisphere of the metal shell. This feature is usually designed so as to cause minimum compromise to the function of the prosthetic hip joint. As a result it is often not strong enough for the impaction forces applied which may result in damage to the insertion tool, the metal shell or both.

As acetabular cups are available in a range of sizes, the tools conventionally used to insert them must similarly be provided in a range of sizes such that they can correctly fit and engage with the features provided on the cups. Having to purchase a range of such tools has cost implications for hospitals.

A third category of prosthetic hip joint exists which is manufactured entirely from metal so that the prosthetic articulation comprises a metal on metal joint. These are usually implanted without cement, relying on a jam fit in the acetabulum. With this type of cup the inner hemisphere is not a convenient place to locate a mechanical feature on which the insertion tool could grip. First, the presence of any mechanical feature on the inner surface would reduce the surface area of the prosthetic articulation. Secondly, it could cause damage to the highly polished surface of the metal.

A further problem which may be encountered is that the forces exerted through the insertion tool during impaction, repositioning and/or extraction may cause the wall of the acetabular cup to be distorted. This is particularly a problem when the cup being inserted, repositioned and/or extracted, is a resurfacing cup since these generally have a thinner wall thickness than standard acetabular cups.

It is therefore desirable to provide an insertion system and in particular an insertion tool for a prosthetic implant in which the attachment means between the insertion tool and the prosthesis is sufficiently robust to withstand the impaction and other forces to which it may be subjected during insertion of the prosthesis and which does not compromise the structural strength or the articulating properties of the prosthesis itself.

One solution to the problems of prior art arrangements is described in GB2323036 in which there is described a prosthetic implant which includes means for attaching a cable to the implant. The cable may secure a liner to the implant. A tool is provided which is connected to the implant by means of the cable. Where the liner is present, the connection of the prosthesis to the tool may be via the liner. In use the surgeon may provide force to the tool to cause the implant to be seated in the bone and then the tool is released. In one arrangement the cable is a continuous cable formed into several loops. Once the prosthesis is located in the desired position, it may be necessary to cut the cable to remove it from the prosthesis.

A second solution to the problems of prior art arrangements is described in EP1634552 in which there is described a cap for use with a prosthesis which is held in place by means of one or more cables and which includes means for cutting the cable and holding the cut cable such that it is removed when the cap is removed. An activation tool comprising a handle, an annular ring to activate the cutting means and an engagement formation is also described.

An alternative approach for securing a bone implant to a tool is described in U.S. Pat. No. 4,677,972. The arrangement described comprises a quick disconnect coupling which links a bone implant to an insertion tool. The coupling includes axially extending undercut teeth which are receivable in corresponding notches formed in the peripheral face of the implant. The teeth are locked in the notches by means of reciprocating slideable shim assemblies.

U.S. Pat. No. 5,904,688 describes a coupling which fits over the surface of an acetabular cup to enable it to interact with an insertion tool. The coupling includes a number of fingers which grip corresponding notches located in the annular face of the cup. Whilst this arrangement may offer certain advantages over prior art systems, it is apparent that the system is only suitable for use with a cup having a significant surface area on the annular face. A similar arrangement is described in U.S. Pat. No. 5,928,287.

An alternative proposal is set out in US 2004/0186586. In the described system, the acetabular cup is provided with angled recesses which are capable of receiving corresponding members located on an insertion and extraction tool.

Whilst these arrangements offer improvements over prior art devices, there is still a need for alternative arrangements and which are preferably usable with thin walled acetabular cups such as resurfacing cups.

The problems associated with prior art arrangements, may be overcome by providing a cap which in use with a prosthesis is held in the prosthesis by lugs suitable to engage recesses in the rim of the prosthesis and which is formed from a plurality of sectors mutually connected at a connection point by respective flanges.

SUMMARY OF THE INVENTION

According to the present invention there is provided a cap for use during the insertion of an acetabular cup prosthesis comprising:

an impaction plate having an upperside and an underside, the impaction plate comprising a plurality of separate sectors mutually connected at a connection point on the impaction plate by means of flanges, each sector including interlocking means which in use enable the impaction plate to be connected to an introduction tool; and at least one lug extending downwardly from the underside of each sector, said lug being located at the portion of the underside of the impaction plate which will in use enable the lug to be interconnected with a corresponding recess on an internal wall, an external wall or a rim of a prosthesis.

The connection point at which the separate sectors are mutually connected is preferably the central point of the impaction plate. A stiffening boss may be provided at the connection point. In one arrangement, the stiffening boss may be located on the undersurface of the cap.

The arrangement of separate sectors mutually connected at a connection point of the impaction plate, means that the cap has some flexibility which enables the cap to be readily connected to, and removed from, the acetabular cup prosthesis. Thus the arrangement allows some flexing of the impact plate. It will be understood that the connection to, and removal from, the acetabular cup prosthesis will involve the insertion of the at least one downwardly extending lug into corresponding depressions in the prosthesis.

The impaction plate may be of any suitable configuration but in one arrangement the sectors will be sized and configured such that in use the impaction plate forms a protective cap over substantially the whole of an open face of the acetabular cup prosthesis but does not impinge on the external surface of the cup and therefore does not hamper the insertion of the prosthesis into the bone. It will be understood that the term "plate" covers all suitable configurations and may include those which have a cross-sectional thickness which varies across the plate. The shape of the plate will generally depend on the specific prosthesis with which the cap is to be used. The impaction plate will generally be of a substantially disk configuration which may sit at least partly in the cup. In a most preferred arrangement, the impaction plate will be circular in shape.

In one arrangement, the edge of the impaction plate will be chamfered. In an alternative arrangement, the impaction plate may include a lip which, in use, extends over at least part of an edge of the prosthesis. The lip may be continuous or, in use, it may extend only over one or more portions of the edge of the prosthesis.

The sectors may be of any suitable configuration. In one arrangement, each sector may be a sector of an annulus. In this arrangement, a flange may extend from a point on the inner radius of the part-annular sector to the connection point. The point from which the flange extends is generally a centre of the inner radius of the part-annular sector.

The impaction plate may include any suitable number of sectors. Generally there will be an even number of sectors. In one preferred arrangement there will be four sectors.

The spacing between the sectors may be the same or different.

In one arrangement of the present invention, each flange connecting a respective sector to the connection point may be configured such that the sectors may move circumferentially. In a preferred embodiment of this arrangement, each flange is configured such that movement of the sectors out of the plane of the cap is minimized. The ability of the sectors to move circumferentially enables the lugs to be readily inserted into the corresponding recesses in an acetabular cup. This arrangement is particularly suitable where the lug is an angled tooth. The circumferential movement allowed by the flange enables the lugs to be snapped into place in corresponding angled recesses in the cup.

In one alternative arrangement, each flange connecting a respective sector to the connection point may be configured such that the sectors may flex out of the plane of the cap. This is a particularly preferred arrangement where the lugs are ribs which are a snap-fit in corresponding recesses in the cup rim.

In a further alternative arrangement, each flange may be configured so that the sectors may move radially to allow the lugs to be moved between a position in which the lugs engage with corresponding recesses in the cup and a position in which the lugs are disengaged from the corresponding recess.

It will be understood that the, or each, flange may be arranged to allow the, or each, sector to have one or more of circumferential movement, radial movement and movement out of the plane.

The lugs may be of any suitable arrangement. They will be situated on the underside of the impaction plate at a point that is suitable to enable them to engage the corresponding recesses located in the rim of the cup prosthesis. The lugs on the respective sectors may be the same or different.

In one arrangement, they will be ribs. The ribs may extend substantially vertically from the impact plate or may be angled thereto. In one arrangement, they will be angled such that the ribs slope inwardly. One or more of the ribs may have a dovetail on at least one end thereof.

In an alternative arrangement, the lugs may be configured such that they are shaped as angled teeth. In one arrangement, the angled teeth on adjacent sectors may be angled in opposing directions. These opposing faced teeth in use serve to assist the connection between the cap and the cup.

However configured, the or each lug may be located in the same position on each sector or may be in different positions. They may be equally spaced.

The impaction plate may be formed from any suitable material. Generally a metal will be used but other materials may be used provided that they have sufficient strength to withstand the impaction and enable the flexibility required for use to be achieved. In addition, the material should be suitable to withstand the sterilization process.

The interlocking means to enable the impaction plate to be connected to an introducer tool may be any suitable means. In one arrangement, the means are one or more apertures extending through each sector. The one or more aperture may be of any suitable configuration. In one arrangement, the interlocking means may allow the cap to be permanently connected to an introducer tool.

According to a second aspect of the present invention there is provided an acetabular cup in combination with the cap of the above first aspect. The cup will include recesses in the rim of the cup into which the lugs extending from the impaction plate can be inserted. In one arrangement, the recesses will be grooves which may be dovetailed at the at least one end. In an alternative arrangement, the recesses may be shaped to receive angled teeth. These recesses may be at least partially undercut into the rim of the cup.

In one arrangement, the acetabular cup is a resurfacing cup.

The cap of the first aspect of one aspect of the present invention is able to grip the cup circumferentially thereby minimizing, and preferably obviating, the risk of distortion of the cup during impaction, repositioning and/or extraction. This arrangement of the present invention avoids applying radial forces against the cup walls which generally lead to distortion thereof.

Generally, the cup is provided to the surgeon with the cap pre-assembled thereon. To assemble the cap onto the cup, each pair of adjacent sectors will be moved apart such that the lugs are engaged in the recesses located in the rim of the cup. It will be understood that once assembled, the cap will remain in position until removed.

The present invention also relates to an introducer tool for use in introducing the acetabular cup prosthesis via the cap of the above-mentioned first aspect.

Thus according to a third aspect of the present invention there is provided an introduction tool comprising a handle, an arm extending from the handle to a foot comprising a fixed component and a movable component, each of said fixed component and said movable component having means for engaging connection means on the impaction plate of the cup of the above-mentioned first aspect of the present invention.

Any suitable tool arrangement of fixed component and movable component may be used. The fixed component may be directly attached to the arm of the tool and the movable component may be attached via a rod to a hinged means on the arm. The rod connecting the movable component to the handle may include articulating means. A portion of the articulation means may provide a second point of contact between the rod and the handle. The articulation means enables the movement of the movable portion of the foot to be generally horizontal, i.e. in the plane of the foot rather than arcuate. This horizontal movement improves the control provided over the foot increasing the ease with which it can be connected to and removed from engagement with the cap. In one arrangement, the tool is configured such that its movement in use decreases any tendency to distort the sectors out of the plane of the cap.

In the arrangement in which the impaction cap includes four sectors each having an aperture therein, the fixed component of the foot will comprise two fingers, one for engaging apertures in each of the two of the sectors and the movable foot will comprise two fingers, one for engaging apertures in the remaining two sectors.

In one arrangement in which the movable component is present, means may be included to move the movable component of the foot from at least a first locked position to a second position where connection or removal of the impaction plate is facilitated. In a further arrangement, the movable foot may have three or four fixed positions, an assembly position at which the tool may be connected to the cap and hence the cup, a clamped position at which the insertion of the prosthesis into the bone may be carried out, a release position in which the impaction cap can be removed from the tool and optionally a clean position. In one arrangement of the present invention, means may be provided for moving the movable component of the foot between the various positions. The means will generally be provided where the rod is hinged to the handle.

Although the tool may be provided in differing sizes, generally a single tool may be used with a variety of cap sizes provided that each cap is provided with the same sized connection means.

Where the cap of the above first aspect has apertures as connection means, the engaging means on the tool will include cooperating fingers which will interlock with the apertures in the cap. The fingers will generally be shaped to better engage the apertures in the cap which may be shaped with cooperating surfaces. For example, in one arrangement, the fingers may be angled from the vertical in order to better engage with the apertures in the cap which may be similarly angled. In one alternative arrangement, the fingers may have a protuberance on at least a portion of it to be a snap-fit in the aperture of the cap. The protuberance may be a ring around the circumference of the finger.

According to a fourth aspect there is provided a kit of parts comprising one or more of the acetabular prosthesis of the above second aspect, one or more caps of the above first aspect of the present invention and at least one introduction tool of the above third aspect.

When used, the cap may be disposable or it may be reusable after appropriate sterilization.

Other features of the invention will be in part apparent and in part pointed out hereinafter.

BRIEF DESCRIPTION OF THE DRAWINGS

The present invention will now be described, by way of example, with reference to the following examples in which:

FIG. 8 represents one example of an introducer tool;

FIG. 9 illustrates the tool, cap and acetabular cup in exploded arrangement;

FIG. 10 is a schematic illustration of a partial cross-section of the cup illustrating the dovetail end of the depression;

Corresponding reference characters indicated corresponding parts throughout the views of the drawings.

DETAILED DESCRIPTION OF THE PREFERRED EMBODIMENTS

Figure 1:
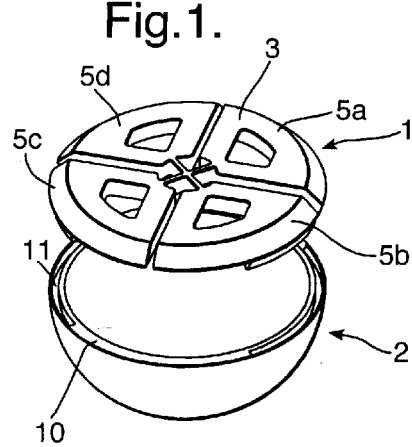
FIG. 1 is a schematic representation of one arrangement of the present invention in combination with an acetabular cup prosthesis.
Figure 2:
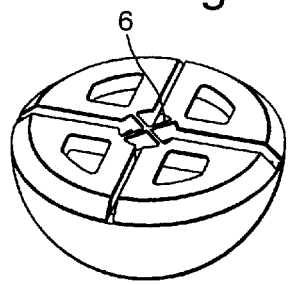
FIG. 2 is a schematic representation of the arrangement of FIG. 1 with the cap in place on the cup.
Figure 3:
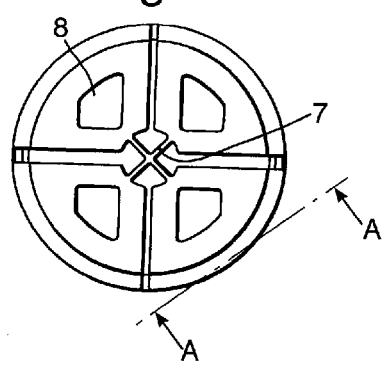
FIG. 3 is a view from above of the cap of FIG. 1.
Figure 5:
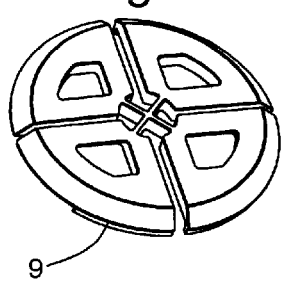
FIG. 5 is a schematic view of the cap of FIG. 1.

As illustrated in FIGS. 1 to 7, a cap 1 is provided for an acetabular cup prosthesis 2. The cap comprises an impaction plate 3 comprising four sectors 5a, 5b, 5c and 5d. Each sector is connected to a connection point 6 via flanges 7.

Each sector includes an aperture 8 which provides means for connecting the cap to an insertion tool.

Figure 6:
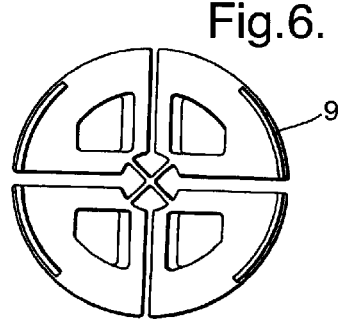
FIG. 6 is a view from below of the cap of FIG. 3.

As illustrated most clearly in FIG. 6, the gaps between the sectors are not equal.

Figure 4:
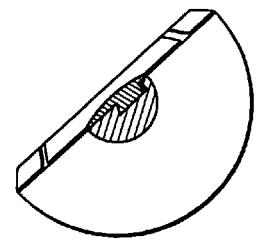
FIG. 4 is a cross-section on the line A-A on FIG. 3.
Figure 7:
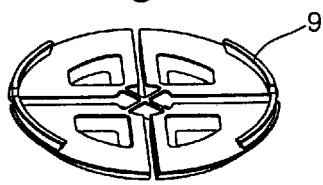
FIG. 7 is a perspective view of the underside of the cap of FIG. 6.

Lugs in the form of ribs 9 extend from each of the sectors. As illustrated in FIG. 7 the ribs are angled inwardly. These ribs are shaped to interact with dovetailed edges to corresponding grooves 11 in the rim 10 of the cup 2. The dovetailed edge is illustrated in FIGS. 4 and 10.

One arrangement of a tool 12 is illustrated in FIG. 8. The tool 12 comprises a handle 13, an arm 14 and a foot 15a and 15b. The foot comprises a fixed component 15a and a movable component 15b. The movable foot component 15b is connected to the arm 14 by means of a rod 16. A locking means 17 enables the rod and hence the movable foot component to be moved.

Fingers 18 extend from each of the foot components. The relationship between these finger components and the apertures 8 in the cap 1 is illustrated in FIG. 9. FIG. 9 also illustrates the relationship between the ribs 9 and the depressions 11.

Figure 11:
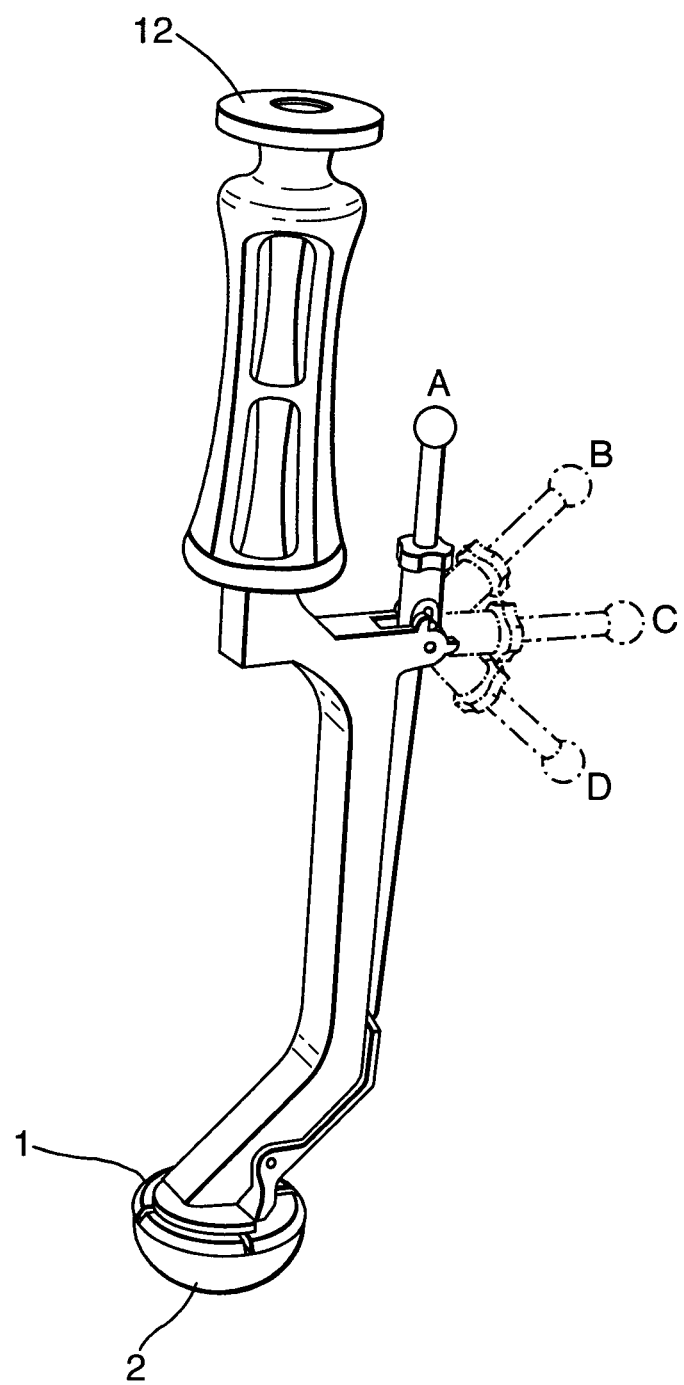
FIG. 11 illustrates the tool in combination with the cap and cup illustrating the four positions of the locking means.

FIG. 11 illustrates the components when combined. When the locking means 17 is in position A, the components of the tool will be locked in the position illustrated in FIG. 11. Positions B to D are merely illustrative as to the position at which the position means can be positioned. It will be understood that the rod, foot etc will move as the locking means is moved between the various positions.

Figure 12:
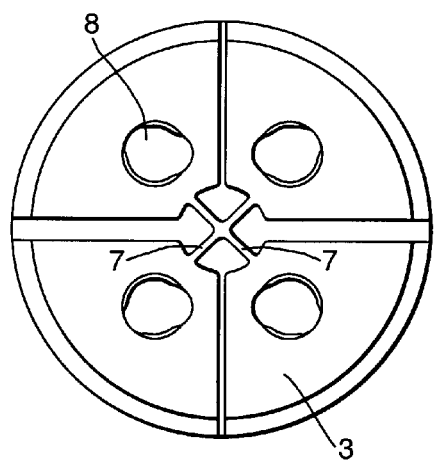
FIG. 12 is a view from above of an alternative arrangement of a cap of the present invention.
Figure 13:
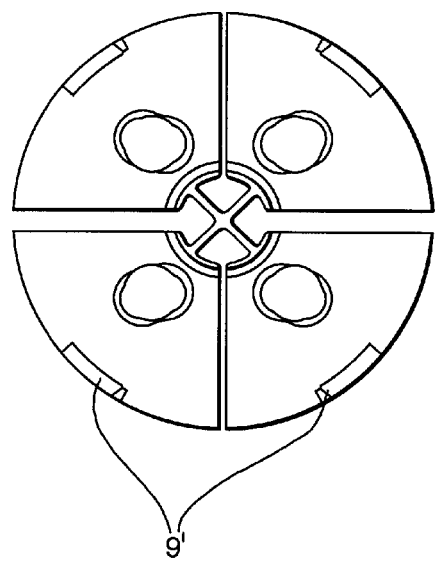
FIG. 13 is an underside view of the cap of FIG. 12.
Figure 14:
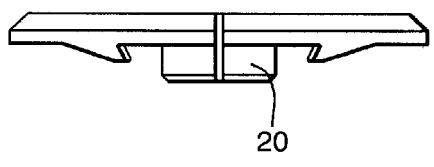
FIG. 14 is a front side view of the cap of FIG. 12.
Figure 15:
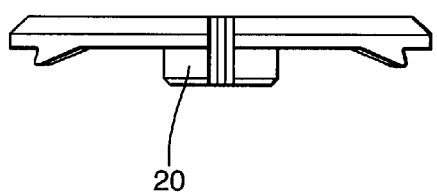
FIG. 15 is a right hand side view of the cap of FIG. 12.

An alternative cap is illustrated in FIGS. 12 to 18. As in the first embodiment, the cap comprises an impaction plate having four sectors. Each sector is connected to a connection point via flanges 7. As illustrated in FIG. 12, the gaps between the sectors are not equal. A stiffening boss 20 is located on the undersurface of the cap.

Apertures 8 are located in sectors to provide means for connecting the cap to an insertion tool.

Figure 16:
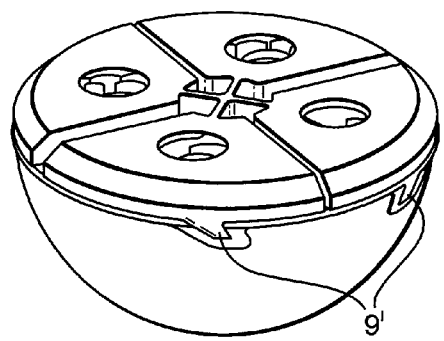
FIG. 16 is a perspective view of the cap of FIG. 12 located on an acetabular cup.
Figure 17:
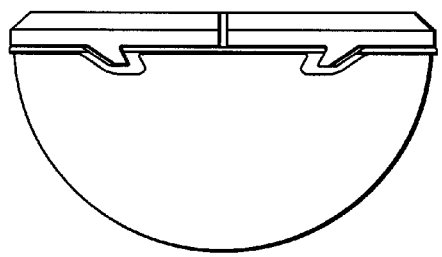
FIG. 17 is a front side view of the arrangement of FIG. 16.
Figure 18:
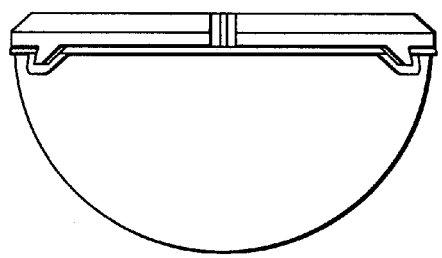
FIG. 18 is a right hand side view of the arrangement of FIG. 16.

Lugs in the form of angled teeth 9' extend from the underside of each sector. The configuration of each tooth is illustrated clearly in FIGS. 14 and 15. A pair of sectors separated by the narrower gap, each have a tooth angled inwardly towards the other. As shown in FIG. 16 in use, these teeth interlock with cooperating recesses in the rim of the acetabular cup and engage therewith. Each recess has an undercut at one end and an opposite angled release surface at the other end. The sectors work together in two pairs about the connection point. Each pair of lugs form a dovetail shape when viewed together. In use the acute angled face of each tooth clamps against a reverse angled aperture in the cup. Thus dovetail lugs engage undercut slots when assembled with the cup. These engaging features are the mechanism by which the impaction plate is connected to the cup and also allow the cup to be controlled by the introducer tool when the cup is attached to the tool.

Figure 19:
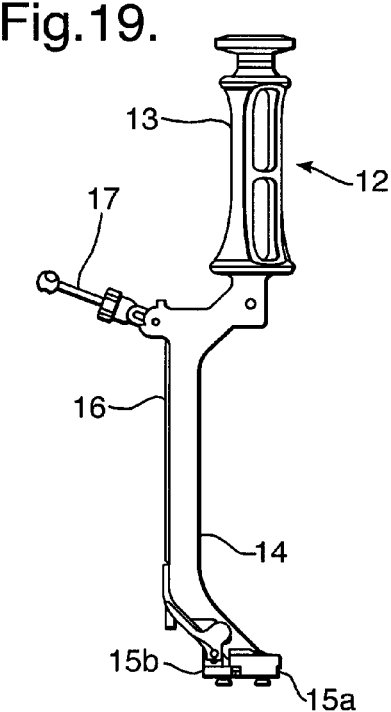
FIG. 19 is an alternative tool of the present invention in assembly mode.
Figure 20:
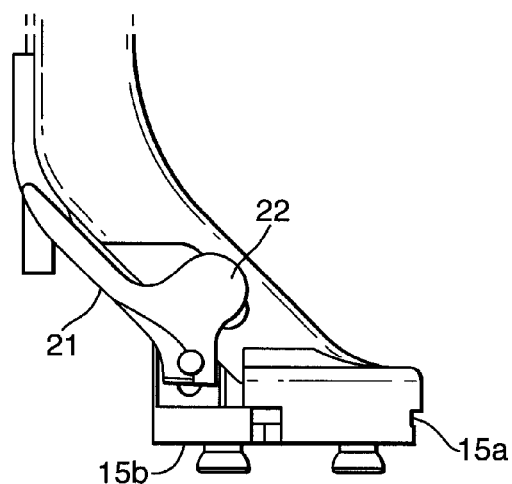
FIG. 20 is an enlarged view of a portion of the tool in assembly mode.

An alternative tool arrangement is described in FIGS. 19 to 26. In this arrangement, the tool 12 comprises a handle 13, an arm 14 and a foot 15a and 15b. The movable foot component 15b is connected to the arm by means of a rod 16. A locking means 17 enables the rod and hence the movable component of the foot to be moved. As illustrated in FIG. 20 an articulation means 21 is provided on the rod above the movable component of the foot. A portion 22 of the articulation is connected to the arm 14. The articulation and its connection to the arm assists the movement of the movable portion of the foot to be controlled.

Figure 21:
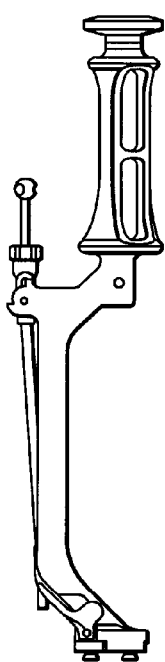
FIG. 21 is a side view of the tool of FIG. 19 in clamping mode.
Figure 22:
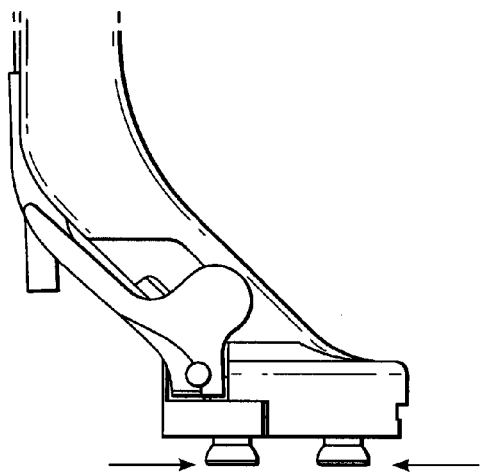
FIG. 22 is an enlarged view of a portion of the tool in clamping mode.
Figure 23:
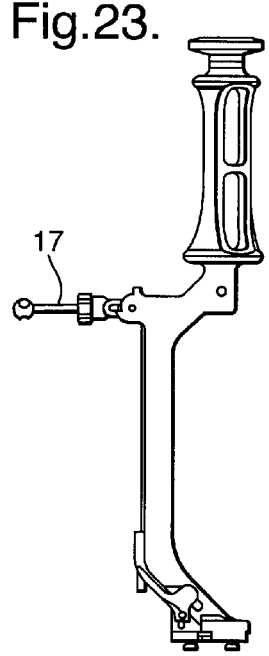
FIG. 23 is a side view of the tool of FIG. 19 in release mode.
Figure 24:
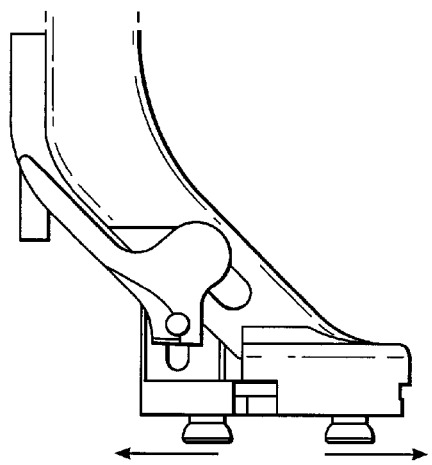
FIG. 24 is an enlarged view of a portion of the tool in release mode.

The tool as illustrated in assembly mode is illustrated in FIGS. 19 and 20. It is in this position that the instrument can be connected to the cap located on the cup. As illustrated in FIGS. 21 to 23, the locking means 17 may then be moved to the clamping position which moves the movable portion of the foot inwardly towards the other portion of the foot. In this arrangement, the fingers are pushed together as illustrated by the arrows to clamp the impaction cap more firmly onto the cap.

Once the surgeon has placed the prosthesis in position, the tool needs to be disengaged from the cap. The locking means 17 is then moved to the position illustrated in FIGS. 23 and 24. In this position, the tool is in the release position. The movable component of the horizontally in the direction illustrated by the arrows in FIG. 24.

Figure 25:
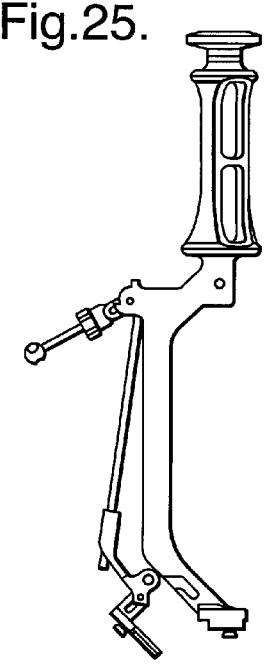
FIG. 25 is a side view of the tool of FIG. 19 in cleaning mode.
Figure 26:
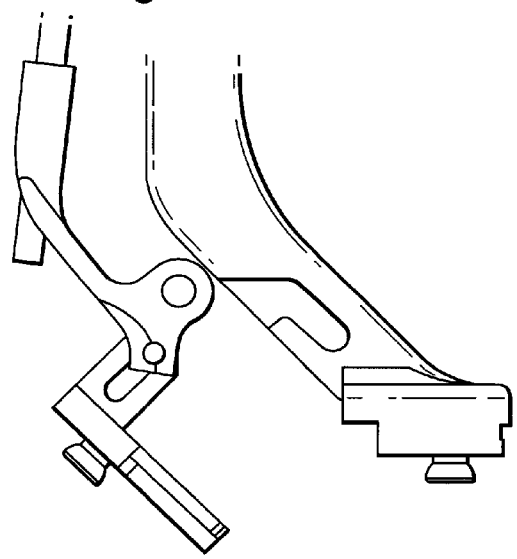
FIG. 26 is an enlarged view of a portion of the tool in cleaning mode.

For cleaning purposes, the locking means 17 may be moved to a fourth position which enables the movable portion of the foot to be separated from the fixed portion such that access to all components is readily achieved. This is illustrated in FIGS. 25 and 26.

Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A cap for use during the insertion of an acetabular cup prosthesis comprising:
   an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;

wherein the connection point at which the separate sectors are mutually connected is a central point of the impaction plate.

2. A cap according to claim 1 wherein a stiffening boss is provided at the connection point.

3. A cap according to claim 1 wherein the impaction plate is sized and configured such that in use the impaction plate forms a protective cap over substantially the whole of an open face of the acetabular cup prosthesis but does not impinge on the external surface of the cup.

4. A cap according to claim 1 wherein the impaction plate is circular in shape.

5. A cap according to claim 1 wherein the impaction plate is chamfered.

6. A cap according to claim 1 wherein each sector is a sector of an annulus.

7. A cap according to claim 1 wherein the impaction plate comprises four sectors.

8. A cap according to claim 7 wherein the spacing between two sectors is different to that between two other sectors.

9. A cap according to claim 1 wherein each flange connecting a respective sector to the connection point is configured such that the sectors move substantially circumferentially.

10. A cap according to claim 1 wherein the cap generally defines a plane, wherein each flange connecting a respective sector to the connection point is configured such that the sectors move out of the plane of the cap.

11. A cap according to claim 1 wherein the lugs on each sector are of the same configuration.

12. A cap according to claim 1 wherein each lug is a rib.

13. A cap according to claim 12 wherein each rib slopes inwardly.

14. A cap according to claim 13 wherein each rib has a dovetail on at least one end thereof.

15. A cap according to claim 1 wherein the or each lug is an angled tooth.

16. A cap according to claim 15 wherein angled teeth on adjacent sectors are angled in opposing directions.

17. A cap according to claim 1 further comprising an aperture extending through each sector enabling the impaction plate to be connected to an introducer tool.

18. A cap according to claim 1 in combination with an acetabular cup prosthesis.

19. The combination according to claim 18 wherein the acetabular cup is a resurfacing cup.

20. The combination according to claim 18 wherein recesses are located in a rim of the cup into which the lugs extending from the impaction plate can be inserted.

21. The combination according to claim 20 wherein the recesses are grooves.

22. The combination according to claim 21 wherein each groove is dovetailed at at least one end.

23. The combination according to claim 20 wherein the recesses are shaped to receive angled teeth and the recesses are at least partially undercut into the rim of the cup.

24. The cap of claim 1 wherein each of the lugs of the plurality of sectors is not disposed within a corresponding recess when the plurality of sectors is in the second position.

25. The cap of claim 1 wherein the plurality of sectors are movable radially between the first position and the second position.

26. The cap of claim 1 wherein the plurality of sectors are movable circumferentially between the first position and the second position.

27. The cap of claim 1 wherein the plurality of sectors, when in the first position, define a first plane, and the plurality of sectors are movable from the first position to the second position, which is out of plane with the first plane.

28. A cap according to claim 1 in combination with an introduction tool,
wherein the cap includes a connection means on the impaction plate of the cap,
wherein the introduction tool comprises a handle, an arm extending from the handle to a foot comprising a fixed component and a movable component, each of said fixed component and said movable component having means for engaging said connection means on the impaction plate of the cap during insertion of an acetabular cup prosthesis.

29. The combination according to claim 28 wherein the movable component is attached via a rod to a hinged means on the arm.

30. The combination according to claim 29 wherein the rod includes articulating means.

31. The combination according to claim 28 wherein the fixed component of the foot comprises at least one finger, and the movable component of the foot comprises at least one finger.

32. The combination according to claim 31 wherein the fixed and movable component each comprises two fingers.

33. A kit of parts comprising:
at least one acetabular cup prosthesis; and
at least one cap according to claim 1.

34. A system for implanting a hip cup, comprising:
a cup having an outer wall having a rim including a plurality of recesses extending into the wall from the surface of the rim; and
an impaction plate having an upperside and an underside, and comprising a plurality of separate sectors mutually connected at a connection point on the impaction plate by flanges, each of the plurality of sectors having an outer edge and an aperture configured to engage an introduction tool in use, the plurality of sectors comprising at least a first sector and a second sector; and
at least one lug extending away from the underside of each sector near the outer edge of each sector, each lug being located such that when in use the lug is positionable at least partially within a corresponding recess of the plurality of recesses, and wherein each of the plurality of sectors is movable between a first position, in which each of the lugs is at least partially disposed within a corresponding recess and the distance measured between an outer edge of a first sector and an outer edge of a second sector is a first distance, and a second position, in which the distance measured between an outer edge of a first sector and an outer edge of a second sector is less than the first distance.

35. The system of claim 34 further comprising a tool having a first foot including at least a first finger, a second foot including at least a second finger, each of said first finger and said second finger being attachable to a separate aperture of the plurality of sectors, and an actuator for moving the first foot and the second foot relative to one another.

36. The system of claim 34 wherein the cup comprises an internal wall and an external wall, and the recess extends from the rim to the external wall.

37. A cap for use during the insertion of an acetabular cup prosthesis comprising:
- an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and
- at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;
- wherein a stiffening boss is provided at the connection point.

38. A cap for use during the insertion of an acetabular cup prosthesis comprising:
- an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and
- at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;
- wherein the impaction plate comprises four sectors.

39. A cap for use during the insertion of an acetabular cup prosthesis comprising:
- an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and
- at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;
- wherein the cap generally defines a plane, wherein each flange connecting a respective sector to the connection, point is configured such that the sectors move out of the plane of the cap.

40. A cap for use during the insertion of an acetabular cup prosthesis comprising:
- an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and
- at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;
- wherein each lug is a rib, wherein each rib slopes inwardly, and each rib has a dovetail on at least one end thereof.

41. A cap in combination with an acetabular cup prosthesis:
the cap comprising:
- an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and
- at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;
- the acetabular cup prosthesis comprising recesses located in a rim of the cup into which the lugs extending from the impaction plate can be inserted.

42. A cap for use during the insertion of an acetabular cup prosthesis comprising:
- an impaction plate having an upperside and an underside, the impaction plate comprising a plurality of separate sectors mutually connected at a connection point on the impaction plate by flanges, each of the plurality of sectors having an outer edge, the plurality of sectors comprising at least a first sector and a second sector; and
- at least one lug extending away from the underside of each sector near the outer edge of each sector, said lug being located at the portion of the underside of the impaction plate which in use will enable the lug to be interconnected with a corresponding recess on an internal wall, an external wall or a rim of a prosthesis; wherein each of the plurality of sectors is movable between a first position, wherein each of the lugs is at least partially disposed within a corresponding recess and the distance measured between an outer edge of a first sector and an outer edge of a second sector is a known distance, and a second position, wherein the distance measured between an outer edge of a first sector and an outer edge of a second sector is less than the known distance;
- the spacing between two sectors is different to that between two other sectors.

\* \* \* \* \*

UNITED STATES PATENT AND TRADEMARK OFFICE
CERTIFICATE OF CORRECTION

| | | |
|---|---|---|
| PATENT NO. | : 8,500,744 B2 | Page 1 of 1 |
| APPLICATION NO. | : 11/383139 | |
| DATED | : August 6, 2013 | |
| INVENTOR(S) | : Wozencroft et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1539 days.

Signed and Sealed this
Tenth Day of February, 2015

Michelle K. Lee
*Deputy Director of the United States Patent and Trademark Office*